United States Patent [19]

Tuompo et al.

[11] Patent Number: 5,786,167
[45] Date of Patent: Jul. 28, 1998

US005786167A

[54] METHOD AND CULTURE MEDIUM FOR IDENTIFICATION OF SALMONELLAE

[75] Inventors: Helena Tuompo; Leena Scheinin, both of Espoo; Marita Jussila, Otalampi; Irmeli Laine, Espoo, all of Finland

[73] Assignee: Orion-Yhtymae Oy, Espoo, Finland

[21] Appl. No.: 737,990

[22] PCT Filed: Mar. 20, 1996

[86] PCT No.: PCT/FI96/00163

§ 371 Date: Nov. 22, 1996

§ 102(e) Date: Nov. 22, 1996

[87] PCT Pub. No.: WO96/30543

PCT Pub. Date: Oct. 3, 1996

[30] Foreign Application Priority Data

Mar. 24, 1995 [FI] Finland ............... 951431

[51] Int. Cl.[6] ............... C12Q 1/04; C12Q 1/54; C12Q 1/34; C12Q 1/02
[52] U.S. Cl. ............... 435/34; 435/14; 435/18; 435/29; 435/30; 435/879; 435/822; 435/968; 426/48; 426/52; 426/55; 426/42; 426/43; 546/152; 436/1.11
[58] Field of Search ............... 435/34, 14, 879, 435/968, 822, 30, 18, 29; 426/48, 52, 55, 42, 43; 546/152; 536/1.11

[56] References Cited

U.S. PATENT DOCUMENTS

| | | | |
|---|---|---|---|
| 3,879,601 | 4/1975 | Warren et al. | 435/34 |
| 3,936,356 | 2/1976 | Janin | 435/34 |
| 3,957,584 | 5/1976 | Kronish et al. | 435/34 |
| 4,279,995 | 7/1981 | Woods et al. | 435/34 |
| 4,308,348 | 12/1981 | Monget | 435/34 |
| 5,098,832 | 3/1992 | Rambach | 435/34 |
| 5,194,374 | 3/1993 | Rambach | 435/34 |
| 5,208,150 | 5/1993 | Tate et al. | 435/34 |
| 5,434,056 | 7/1995 | Monget et al. | 435/14 |
| 5,541,082 | 7/1996 | Botchner | 435/34 |

FOREIGN PATENT DOCUMENTS

| | | |
|---|---|---|
| 0 326 635 | 8/1989 | European Pat. Off. |
| 92/12259 | 7/1992 | WIPO |
| 94/09152 | 4/1994 | WIPO |
| 94/28163 | 12/1994 | WIPO |

OTHER PUBLICATIONS

Abstract of WO 93/23527 A1, Nov. 25, 1993.

Primary Examiner—Louise N. Leary
Attorney, Agent, or Firm—Evenson, McKeown, Edwards & Lenahan, P.L.L.C.

[57] ABSTRACT

The invention comprises a culture medium and method for distinguishing bacteria of Salmonella species from other gram-negative bacteria, especially those belonging to the family Enterobacteriaceae. It is based on the ability of salmonellae to utilize melibiose, mannitol, and sorbitol and convert them into acids, together with a chromogenic substrate used for identifying β-galactosidase. Other bacteria of the family Enterobacteriaceae, most of which are β-galactosidase-positive, appear as brown, blue, or green colonies, depending on the chromogenic substrate used. Apart from Salmonella species, other β-galactosidase-negative bacteria, such as Proteus species, appear as colorless colonies. Salmonellae can be identified directly on the culture medium after incubation, by their characteristic bright red color.

27 Claims, No Drawings

METHOD AND CULTURE MEDIUM FOR IDENTIFICATION OF SALMONELLAE

BACKGROUND OF THE INVENTION

1. Field of the Invention

The present invention relates to a method and a culture medium for the identification and distinguishing of *Salmonella sp.* among other gram-negative bacteria, especially those belonging to the family Enterobacteriaceae, in an analytical sample. The invention is characterized by the features defined in the claims.

2. Description of Related Art

Rapid species identification of infective organisms is important, whether for epidemiology studies, for diagnosis of both human and veterinary diseases, for selecting appropriate medical treatment or for deciding on control measures in the food industry and other segments of environmental hygiene. To prevent outbreaks of food poisoning, food and environmental (water, soil and alike) samples are continuously being monitored especially for the presence of salmonellae.

At least eight different agar-based media for culturing and identification of salmonellae are commercially available today (Difco Manual, 1984, Difco Laboratories, Detroit, Mich., USA). Most of these are based on determination of lactose utilization and/or measurement of hydrogen sulfide production. Since most salmonellae are lactose-negative and thus do not contain β-galactosidase enzyme as most of the other bacteria in the family Enterobacteriaceae do, they can easily be distinguished from many other bacteria on the basis of their β-galactosidase negativity.

The currently used culture media contain various amounts of additives that inhibit the growth of other bacteria; in other words, the media have been made selective so that only salmonellae would grow on them. These media have many limitations, however. Use of inhibitors that prevent the growth of gram-negative bacteria is undesirable, since some inhibitors will, to some extent, prevent even the growth of salmonellae. In other words, such media are too selective and therefore two different media have to be used, one of which is less selective. The more selective culture medium is used for measuring the production of hydrogen sulfide, which alone is not a reliable method because it is sensitive to many external factors, such as oxygen concentration and pH. Furthermore, several strains produce different amounts of hydrogen sulfide. Combining measurement of hydrogen sulfide production with lactose fermentation on a less selective medium is also insufficient to distinguish salmonellae from other bacteria occurring in nature. Since for example *Proteus spp.* resemble salmonellae in being lactose-negative and in producing hydrogen sulfide, they cannot be distinguished from salmonellae by means of commercial culture media (Difco Manual).

The aforementioned commercial culture media do not allow differentiation among colonies on the basis of appearance, since bacteria form colonies of uniform color on these media. Nevertheless, the recently introduced Rambach agar has been developed with a view to enhancing the distinction of different bacteria directly on the basis of colony color (E. Merck, Darmstadt, Germany). On this agar, *Salmonella spp.* grow as pink colonies while other bacteria of the family Enterobacteriaceae, e.g., many coliforms, form blue, green, violet, or colorless colonies. This advantage of Rambach agar is based on the ability of β-galactosidase-negative salmonellae to utilize propylene glycol. In the presence of an indicator substance, decomposition of propylene glycol yields a red color, and not blue, for instance. Rambach agar is very specific for all salmonella strains except *S. typhi* and *S. paratyphi*. Few false positives are obtained with Rambach agar (Garrick R. G. and A. D. Smith, Letters Appl. Microbiol. 18:187–189, 1994). Still, the method has the disadvantage of not revealing *typhi* strains.

U.S. Pat. No. 5,434,056 discloses a method for selective detection of salmonella, and a medium for that purpose which contains glucuronic acid or its salts, a pH indicator, a chromogenic compound to distinguish β-galactosidase-positive bacteria from β-galactosidase-negative salmonellae, and optionally at least one fermentable sugar. Sugars mentioned include melibiose, sorbitol, dulcitol, mannitol, glucose and glucuronate in concentrations between 1 to 10 g/l. The *Salmonella sp.* are detected as red colonies, the color formation being based on the capacity of salmonella to ferment glucuronic acid or its salts. This method has the disadvantage that *S. arizonae* cannot be distinguished. Further, it is stated in the patent that adding sorbitol to the culture medium may reveal bacteria of the Serratia genus to be false positives. This leads away from using sugars in the medium, and thus it leads away from the present invention.

Biochemical reactions other than those mentioned above can also be used for rapid identification of salmonellae in biological specimens. These reactions include methods based on the utilization of sugars and sugar alcohols, such as bacterial identification by means of melibiose, mannitol, and sorbitol (Bergey's Manual of Systematic Bacteriology, Vol. 1, p. 408, eds. R. G. E. Murray et al., William & Wilkins, Baltimore, USA, 1984).

SUMMARY OF THE INVENTION

We have now developed a medium which contains a pH-indicator, a chromogenic compound to distinguish β-galactosidase-positive bacteria from for example β-galactosidase-negative salmonellae, and a combination of three very carefully selected sugars, i.e. melibiose, mannitol and sorbitol. We have shown that one of these sugars is not sufficient to reliably distinguish all salmonellae as bright red colonies (see Experimental). All three of these sugars are needed to give a reliable result. We have also found that even strains of *Salmonella typhi* can be identified by the new medium now developed, since they utilize mannitol and sorbitol.

Utilization of melibiose, mannitol, and sorbitol in combination with the lack of β-galactosidase activity distinguishes salmonellae from other members of the family Enterobacteriaceae. Addition of a pH indicator, such as neutral red, to the agar makes salmonellae stain bright red when producing acid from melibiose and sugar alcohols. The acids lower the pH around the colonies of *Salmonella spp.*, and only the salmonellae appear as bright red colonies in the presence of neutral red. Characteristically, other β-galactosidase-negative bacteria of the family Enterobacteriaceae, e.g., strains of *Proteus sp.*, appear colorless on the culture medium because they do not utilize melibiose or the above-mentioned sugar alcohols. The β-galactosidase-positive bacteria of Enterobacteriaceae stain differently from salmonellae. In the method presented by us, they stain brown with the use of the chromogenic 8-hydroxyquinoline-β-D-galactoside, a substrate measuring galactosidase activity.

In order to inhibit the growth of gram-positive bacteria it is preferable to use in the culture medium inhibitory substances such as bile salts or anionic detergents. Sodium dodecyl sulphate and 3,9-diethyl-6-tridecanol sulphate ester are examples of suitable anionic detergents.

An analytical sample which can be assayed using the method according to the present invention can be taken from any organ of the human or animal body. Most frequently salmonella is found in the intestinal canal.

However, the occurrence of salmonella has been reported also in many other organs. Representative body fluids may be, for example, feces, urine, abscess, blood, plasma, serum, liquor, bile fluid, healing wound fluid, ascitic fluid, pleural fluid, synovial fluid, blister fluid, or amniotic fluid. A sample may also be any food, environmental, or industrial specimen.

The method developed by us has the further asset of allowing all ingredients of the culture medium to be premixed to yield a powdered medium, i.e., an instant powder mixture, which only requires addition of water before autoclaving and pouring into Petri dishes. Other corresponding products on the market do not permit pre-mixing of all their components to yield a powdered medium. Rambach agar, for example, consists of a powder and a liquid, propylene glycol. Another asset of our method is the stability of the powdered culture medium. The culture medium keeps at least for seven months. If packed well, it also keeps in the form of reconstituted medium, either as plates or dip-slides. The stability of dip-slides is at least six months, when properly stored. The 8-hydroxyquinoline-$\beta$-D-galactoside exhibits especially good stability, unlike other chromogenic substances, such as the chromogenic indole substrate used in Rambach agar.

The invention will be described in detail with the Examples below. The specific examples are provided as a guide to assist in the practice of the invention, and are not intended as a limitation on the scope thereof.

DETAILED DESCRIPTION AND SPECIFIC EMBODIMENTS OF THE INVENTION

Example 1

The experiments were conducted with bacteria representing clinical strains commonly encountered in diarrheal diseases. The salmonella strains (212 strains) and their identification and typing data were obtained from the Department of Special Bacterial Pathogens, National Public Health Institute, Finland. Of the salmonellae, 100 belonged to the group *Salmonella enterica* ssp. *enterica* (serotypes Enteritidis, Typhimurium, and Infantis), which comprises some of the most common bacterial strains in diarrheal diseases. The remaining 112 strains belonged to several other serotypes of salmonella. The development of the culture medium and method also made use of the following type strains of the American Type Culture Collection (ATCC): gram-negative bacteria, including *Salmonella typhimurium* (ATCC 14028), *Escherichia coli* (ATCC 27922), *Klebsiella pneumoniae* (ATCC 13883), *Proteus mirabilis* (ATCC 12453), *Pseudomonas aeruginosa* (ATCC 27853), and *Enterobacter aerogenes* (ATCC 13048); gram-positive bacteria, including *Staphylococcus aureus* (ATCC 25922), *Staphylococcus saprophyticus*, *Staphylococcus epidermidis*, *Streptococcus agalactiae*, *Streptococcus faecium* (ATCC 9790), $\beta$-hemolytic *Streptococcus sp.* of group B, *Enterococcus sp.*, and *Corynebacterium sp.*

The bacteria were grown in Brain Heart Infusion broth (BHI, Difco, Detroit, Mich., USA) at 37° C. for 24 hours. The bacterial concentration was adjusted to $10^8$ bacteria/ml by diluting the BHI with sterile 0.9% NaCl. This suspension was diluted further with 0.9% NaCl. The dilutions were inoculated onto the solid agar-based culture medium of the present invention and the composition of which is presented in Table 1. The culture medium of the present invention is characterized, inter alia, by the fact that it contains, in addition to established components, mannitol, melibiose, sorbitol, and 8-hydroxyquinoline-$\beta$-D-galactoside. The inoculated bacteria were incubated at 37° C. for 24 to 48 hours. The bacterial count of the inoculants was confirmed by culturing the dilution series on a general culture medium without selective substances, e.g., on nutrient agar; the bacterial count was obtained from the colony count/ml.

TABLE 1

| Composition of the culture medium, pH 7.5–8.0. | |
| --- | --- |
| Nutrients and other additives | Amount, g/l |
| Tryptone (Difco) | 15.0 |
| Soybean peptone (Oxoid) | 5.0 |
| Mannitol (Fluka) | 10.0 |
| Melibiose (Fluka) | 10.0 |
| Sorbitol (Fluka) | 10.0 |
| Agar agar (Oxoid) | 22.0 |
| Bile salts (BBL) | 1.8 |
| 8-hydroxyquinoline-$\beta$-D-galactoside (Biosynth) | 0.5 |
| Ferric citrate (Merck) | 1.0 |
| Neutral red (Merck) | 0.02 |
| Distilled water | 1000 ml |

The culture medium may have a pH of 7.5 to 8.0, preferably 7.8 to 8.0.

Example 2

The ingredients listed in Table 1 were weighed, mixed in distilled water, dissolved by heating, and autoclaved at 121° C. for 15 min, after which the agar mixture was poured into Petri dishes. The bacteria were pre-cultured in suspension and diluted to a suitable concentration as set out in Example 1.

As seen in Table 2, the gram-negative bacteria grew equally well on the culture medium of the invention as on the nutrient agar. In addition, the table shows that the growth of gram-positive bacteria was inhibited by the bile salts. Only *Salmonella typhimurium* appeared as red colonies, whereas the colonies of the other $\beta$-galactosidase-negative species, *Proteus mirabilis* and *Pseudomonas aeruginosa*, were colorless. $\beta$-galactosidase-positive coliforms, such as *Escherichia coli* and *Klebsiella pneumoniae*, appeared as brown colonies on the culture medium.

TABLE 2

| Color and bacterial count of colonies of gram-negative and gram-positive bacteria on a culture medium according to Table 1, compared with nutrient agar | | | |
| --- | --- | --- | --- |
| | NEW CULTURE MEDIUM | | NUTRIENT AGAR |
| BACTERIUM | bact/ml | Color of colonies | bact/ml |
| Gram-negative bacteria: | | | |
| *Salmonella typhimurium* (ATCC 14028) | $10^5$ | red | $10^5$ |
| *Escherichia coli* (ATCC 27922) | $10^5$ | brown | $10^5$ |

TABLE 2-continued

Color and bacterial count of colonies of gram-negative and gram-positive bacteria on a culture medium according to Table 1, compared with nutrient agar

| BACTERIUM | NEW CULTURE MEDIUM bact/ml | Color of colonies | NUTRIENT AGAR bact/ml |
|---|---|---|---|
| *Klebsiella pneumoniae* (ATCC 13883) | $10^5$ | brown | $10^5$ |
| *Proteus mirabilis* (ATCC 12453) | $10^5$ | colorless | $10^5$ |
| *Pseudomonas aeruginosa* (ATCC 27853) | $10^5$ | brown | $10^5$ |
| *Enterobacter aerogenes* (ATCC 13048) | $10^5$ | brown | $10^5$ |
| Gram-positive bacteria: | | | |
| *Staphylococcus aureus* (ATCC 25922) | 0 | | $10^5$ |
| *Staphylococcus saprophyticus* | 0 | | $10^5$ |
| *Staphylococcus epidermidis* | 0 | | $10^5$ |
| *Streptococcus agalactiae* | 0 | | $10^5$ |
| *Streptococcus faecium* (ATCC 9790) | 0 | | $10^5$ |
| *Streptococcus* sp., group B | 0 | | $10^5$ |
| *Enterococcus* sp. | 0 | | $10^5$ |
| *Corynebacterium* sp. | 0 | | $10^5$ |

Example 3

Table 3 shows the growth data and color reactions of gram-negative bacteria on the culture medium of the present invention.

TABLE 3

Numbers of bacterial strains tested and the colors of their colonies on the culture medium.

| | Number of strains | Bright red colonies | Brown colonies | Colorless colonies |
|---|---|---|---|---|
| Salmonella sp. | 213 | 211 | 2** | 0 |
| Other members of the family Enterobacteriaceae: | | | | |
| *Escherichia coli* | 33 | 0 | 33 | 0 |
| Proteus sp. | 13 | 0 | 0 | 13 |
| Klebsiella sp. | 8 | 2* | 6 | 0 |
| Enterobacter sp. | 3 | 0 | 3 | 0 |
| Citrobacter sp. | 2 | 0 | 2 | 0 |
| Serratia sp. | 1 | 0 | 0 | 1 |

*pink colony
**β-galactosidase-positive strain

As can be seen in the table, 211 strains of *Salmonella sp.* formed bright red colonies and two strains of *Klebsiella sp.* formed pink colonies on the culture medium of the invention. Two salmonella strains were β-galactosidase-positive and formed brown colonies, as did other β-galactosidase-positive bacterial strains, including *Escherichia coli*. β-galactosidase-negative bacteria, such as *Proteus sp.* and *Serratia sp.*, formed colorless colonies.

Example 4

Comparison was made by cultivating different salmonella strains on media containing one or more of the three substances: mannitol, melibiose and sorbitol.

The results are given in the Table 4. It can be seen that when a combination of mannitol and sorbitol is used only 72% of salmonellae is distinguished as red colonies, whereas a combination of melibiose and sorbitol results in 59% of red salmonellae colonies. When, according to the present invention, a combination of mannitol, sorbitol and melibiose is used, 100% of the cultured salmonellae results in red colonies. The optimal sugar concentrations used are about 10 g/l of each sugar. This is an essential improvement compared to methods of the prior art.

TABLE 4

Performance (colour reaction) of salmonella strains with different sugars on the salmonella medium

| Strains tested (n) | Mannitol + Melibiose n (%) | Melibiose + Sorbitol n (%) | Mannitol + Melibiose + Sorbitol n (%) |
|---|---|---|---|
| 50 | | | |
| Bright red colony | 36 (72) | | 50 (100) |
| Yellow colony | 14 (28) | | |
| 105 | | | |
| Bright red colony | | 62 (59) | 105 (100) |
| Yellow colony | | 43 (41) | |

We claim:

1. A method for distinguishing bacteria of Salmonella species from other bacteria of the family Enterobacteriaceae, comprising plating an analytical sample on a solid medium comprising melibiose, mannitol, sorbitol, a pH indicator, and a chromogenic substrate revealing all β-galactosidase-positive bacteria, and cultivating the bacteria in the sample, whereby the bacteria of Salmonella species appear as bright red colonies.

2. The method according to claim 1, wherein the chromogenic substrate is 8-hydroxyquinoline-β-D-galactoside.

3. The method according to claim 1, wherein the medium further comprises one or more substances that inhibit the growth of gram-positive bacteria.

4. The method according to claim 3, wherein the one or more substances are selected from the group consisting of bile salts and anionic detergents.

5. The method according to claim 1, wherein neutral red is used as the pH indicator.

6. The method according to claim 1, wherein the analytical sample is a body organ or body fluid sample, or a food, environmental, or industrial specimen.

7. A solid culture medium for distinguishing bacteria of Salmonella species from other bacteria of the family Enterobacteriaceae, comprising melibiose, mannitol and sorbitol, a chromogenic substrate that reveals all β-galactosidase-positive bacteria, a pH indicator, and solidification agents and growth factors.

8. The culture medium according to claim 7 wherein the chromogenic substrate is 8-hydroxyquinoline-β-D-galactoside.

9. The culture medium according to claim 7, further comprising one or more substances that inhibit the growth of gram-positive bacteria.

10. The culture medium according to claim 9, wherein the inhibitory substances are selected from bile salts and anionic detergents.

11. The culture medium according to claim 7, wherein the pH of the culture medium is 7.5 to 8.0.

12. The culture medium according claim 7, wherein the culture medium is in powdered form.

13. The culture medium according to claim 7, wherein the medium is in a prepared form.

14. The culture medium according to claim 8, wherein the medium is in a prepared form.

15. The culture medium according to claim 9, wherein the medium is in a prepared form.

16. The culture medium according to claim 10, wherein the medium is in a prepared form.

17. The culture medium according to claim 11, wherein the medium is in a prepared form.

18. The culture medium according to claim 8, wherein the medium is in powdered form.

19. The culture medium according to claim 9, wherein the medium is in powdered form.

20. The culture medium according to claim 10, wherein the medium is in powdered form.

21. The culture medium according to claim 11, wherein the medium is in powdered form.

22. The culture medium according to claim 8, further comprising one or more substances that inhibit the growth of gram-positive bacteria.

23. The method according to claim 2, wherein the medium further comprises one or more substances that inhibit the growth of gram-positive bacteria.

24. The method according to claim 2, wherein the analytical sample is a body organ or body fluid sample, or a food, environmental, or industrial specimen.

25. The method according to claim 3, wherein the analytical sample is a body organ or body fluid sample, or a food, environmental, or industrial specimen.

26. The method according to claim 4, wherein the analytical sample is a body organ or body fluid sample, or a food, environmental, or industrial specimen.

27. The method according to claim 5, wherein the analytical sample is a body organ or body fluid sample, or a food, environmental, or industrial specimen.

* * * * *